(12) United States Patent
Takahashi

(10) Patent No.: US 8,790,349 B2
(45) Date of Patent: Jul. 29, 2014

(54) AUTOLOGOUS BONE COLLECTION DEVICE HAVING ENHANCED SUCTION EFFICIENCY

(76) Inventor: Atsushi Takahashi, Tsuruga (JP)

( * ) Notice: Subject to any disclaimer, the term of this patent is extended or adjusted under 35 U.S.C. 154(b) by 1860 days.

(21) Appl. No.: 11/908,677

(22) PCT Filed: Mar. 14, 2006

(86) PCT No.: PCT/JP2006/304945
§ 371 (c)(1),
(2), (4) Date: Sep. 14, 2007

(87) PCT Pub. No.: WO2006/098293
PCT Pub. Date: Sep. 21, 2006

(65) Prior Publication Data
US 2009/0306669 A1 Dec. 10, 2009

(30) Foreign Application Priority Data

Mar. 15, 2005 (JP) .................. 2005-073101

(51) Int. Cl.
*A61F 5/00* (2006.01)
*A61C 17/08* (2006.01)
*A61C 17/06* (2006.01)
*A61C 1/00* (2006.01)
*A61B 10/02* (2006.01)
*A61M 1/00* (2006.01)

(52) U.S. Cl.
CPC ............ *A61M 1/0056* (2013.01); *A61B 10/025* (2013.01); *A61C 17/043* (2013.01); *A61M 1/008* (2013.01); *A61M 17/1635* (2013.01); *A61C 1/0076* (2013.01)

USPC ............................ 606/86 R; 433/92; 600/562

(58) Field of Classification Search
USPC ...................... 128/DIG. 18; 285/381.1–381.5; 433/91–92, 95; 600/562–565, 571; 604/902, 413; 606/79, 127–128, 86 R; 210/106–107, 172.3, 413
See application file for complete search history.

(56) References Cited

U.S. PATENT DOCUMENTS

| | | | | |
|---|---|---|---|---|
| 2,089,702 | A * | 8/1937 | Lomax | 210/408 |
| 4,003,837 | A * | 1/1977 | Osborne | 210/408 |
| 4,281,841 | A * | 8/1981 | Kim et al. | 277/625 |
| 5,630,939 | A * | 5/1997 | Bulard et al. | 210/416.1 |
| 5,741,397 | A * | 4/1998 | Kraver | 159/25.2 |
| 6,183,254 | B1 * | 2/2001 | Cohen | 433/92 |
| RE38,018 | E * | 3/2003 | Anctil et al. | 606/170 |
| 6,626,890 | B2 * | 9/2003 | Nguyen et al. | 604/542 |
| 7,214,059 | B2 * | 5/2007 | Takahashi | 433/92 |
| 7,621,917 | B2 * | 11/2009 | Geneve et al. | 606/86 R |
| 2004/0097829 | A1 * | 5/2004 | McRury et al. | 600/564 |

* cited by examiner

Primary Examiner — Nicholas Woodall
Assistant Examiner — Larry E Waggle, Jr.

(57) ABSTRACT

A bone piece collector wherein a blade (4) coming into tight contact with the surface of a filter (2) under an appropriate pressure is provided in order to prevent lowering in the efficiency of suction work due to sampled bone chips adhering to the surface of the filter (2) in the bone piece collector provided in a suction line in order to sample a bone, i.e. a transplantation material in autologous bone transplantation, the blade (4) is rotated while being pressed against the surface of the filter (2) with a finger pressure or a motor drive force, and the sampled bone chips are moved in a certain direction so that clogging of the filter (2) is eliminated and the suction efficiency can be recovered at any time.

9 Claims, 5 Drawing Sheets

AUTOLOGOUS BONE COLLECTION DEVICE HAVING ENHANCED SUCTION EFFICIENCY

BACKGROUND OF THE INVENTION

1. Field of the Invention

The present invention relates to an autologous bone collection device, and in particular, to an autologous bone collection device for collecting bones cut off during a surgical operation or selectively collecting bone speckles from a non-implant site.

2. Description of the Related Art

In a conventional autologous bone implantation operation, speckles of bone may be cut off by a cutting tool for a head surgery operation due to a defective portion caused by congenital malformation or trauma and then re-implanted to the same portion. Speckles of bone may also be cut off from an implant cavity formed in the jawbone and used for implantation elsewhere. In the latter example, the cooling water injected by a turbine, saliva, blood and speckles of bone cut from bones are selectively collected by a filter disposed on a suction nozzle side of a vacuum device for re-implantation. When the described device is, however, used to collect a large amount of speckles of bone, the objects which are suctioned often stack on the filter to obstruct the mesh of the filter, which causes low operational efficiency or reverse liquid flow. Although a filter with a larger mesh may have higher suction efficiency, due to the larger mesh, the smaller speckles of bone are suctioned out of the filter along the vacuum path, which causes lower collection amount and discarded speckles of bone. The speckles of bone are stacked on the filter wall to be collected. Meanwhile, although tools used in surgery should not be repeatedly used due to protein residual, they are, however, frequently re-used after sterilization.

As described above, to collect the largest amount of speckles of bone from the smallest area for minimal surgical invasiveness, a filter having a mesh is efficient in collecting the most speckles of bone. However, when a small mesh is utilized, the filter is easily obstructed by the speckles of bone during collection, which causes low suction efficiency. Therefore, an efficient method for frequently exchanging the filter during surgical operations or removal of obstructions/speckles of bone stacked on the surface of the filter is needed.

BRIEF SUMMARY OF INVENTION

The invention provides an autologous bone collecting device with constant suction efficiency. When the speckles of bone are collected by a filter (with or without a small mesh), the desired amount of speckles of bone is easily collected without exchanging or cleaning the filter during the surgical operation. Additionally, obstructions/speckles of bone stacked on the surface of the filter are moved to an arbitrary position, whereby the suction efficiency is maximized.

An embodiment of the autologous bone collection device with constant suction efficiency comprises a suction nozzle side connected to a suction nozzle to suction speckles of bone and objects along a suction path, a main body having a base detachably connected to the end of the suction nozzle side. The suction nozzle side and the base extend to a separated portion of the main body. The base is detachably disposed and rotatably on the suction nozzle side but not rotatably on the base side. The autologous bone collection device with constant suction efficiency has a blade fixed to the suction nozzle side of the main body. The blade has a spiral shape with respect to the axis of the main body.

When the filter collects speckles of bone, the speckles of bone and objects separate from liquids to remain on the surface of the filter which may obstruct the filter causing decrease of suction efficiency. The base connected to the filter by an anti-rotation device is manually held, and the suction nozzle side having a blade fixed thereon, is rotated manually, allowing the blade to move the speckles of bone stacked on the surface of the filter to the bottom of the filter.

Another embodiment of an autologous bone collection device with constant suction efficiency of the invention discloses an autologous bone collection device comprising a motor rotating the blade in a predetermined direction to move obstructions/speckles of bone to the bottom of the filter.

An embodiment of an autologous bone collection device with constant suction efficiency of the invention discloses an autologous bone collection device comprising a gap between the blade and the inner wall of the filter to form a guiding angle for obstructions/speckles of bone, whereby the obstructions/speckles of bone are moved to an arbitrary position in the filter by rotation of the blade.

Yet another embodiment of an autologous bone collection device with constant suction efficiency of the invention discloses an autologous bone collection device comprising a main body partially or entirely covered by a shrink film to prevent junction air leaking, wherein the shrink film does not obstruct the rotation of the blade. The main body has an air leak hole integrally formed with the main body and covered by the shrink film.

The autologous bone collection device with constant suction efficiency of the invention suctioning objects from a suction path is provided. Suction efficiency of a filter is affected by obstructions/speckles of bone stacked on the surface of the filter during the collection procedure. Speckles of bone larger than a mesh of the filter collect on the inner wall of the filter and are tightly stacked thereon, which causes the obstructions of the filter. In such a condition, the main body is dissembled to move the collected speckles of bone stacked on the surface of the filter to another container without pollution and change the filter. In an embodiment of an autologous bone collection device with constant suction efficiency of the invention, the speckles of bone stacked on the surface of the filter is moved to the bottom of the filter for collection by rotating a blade contacting the filter manually, by holding the base steady and rotating the suction nozzle side of the device.

In another embodiment of an autologous bone collection device with constant suction efficiency of the invention, the blade is rotated by a motor in a predetermined direction to avoid obstructions/speckles of bone being stacked on the surface of the filter, which would decrease suction efficiency, and move the obstructions/speckles of bone to the bottom of the filter. In the embodiment, the blade can rotate constantly or frequently to provide constant suctions efficiency. In the embodiment of an autologous bone collection device with constant suction efficiency of the invention, the contact angle of the blade and the filter moves the speckles of bone in a predetermined direction to be stacked in a gap between the blade and the filter, thus, facilitating removal of the speckles of bone from the filter.

In yet another embodiment of an autologous bone collection device with constant suction efficiency of the invention, an air leak hole is formed on the main body to prevent junction air leakage. Additionally, the main body is partially or entirely covered by a shrink film, wherein the shrink film does not obstruct the rotation of the blade. However, when the autologous speckles of bone are collected, the filter must be removed, thus, possibly damaging the shrink film and the main body if no pressure within shrink film area is released.

Therefore, when the filter is removed and the speckles of bone are collected, the air leak hole allows air pressure within the shrink film area to be released, thus, preventing possible damage and allowing for repeated usage.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein.

DETAILED DESCRIPTION OF INVENTION

Figure 1:
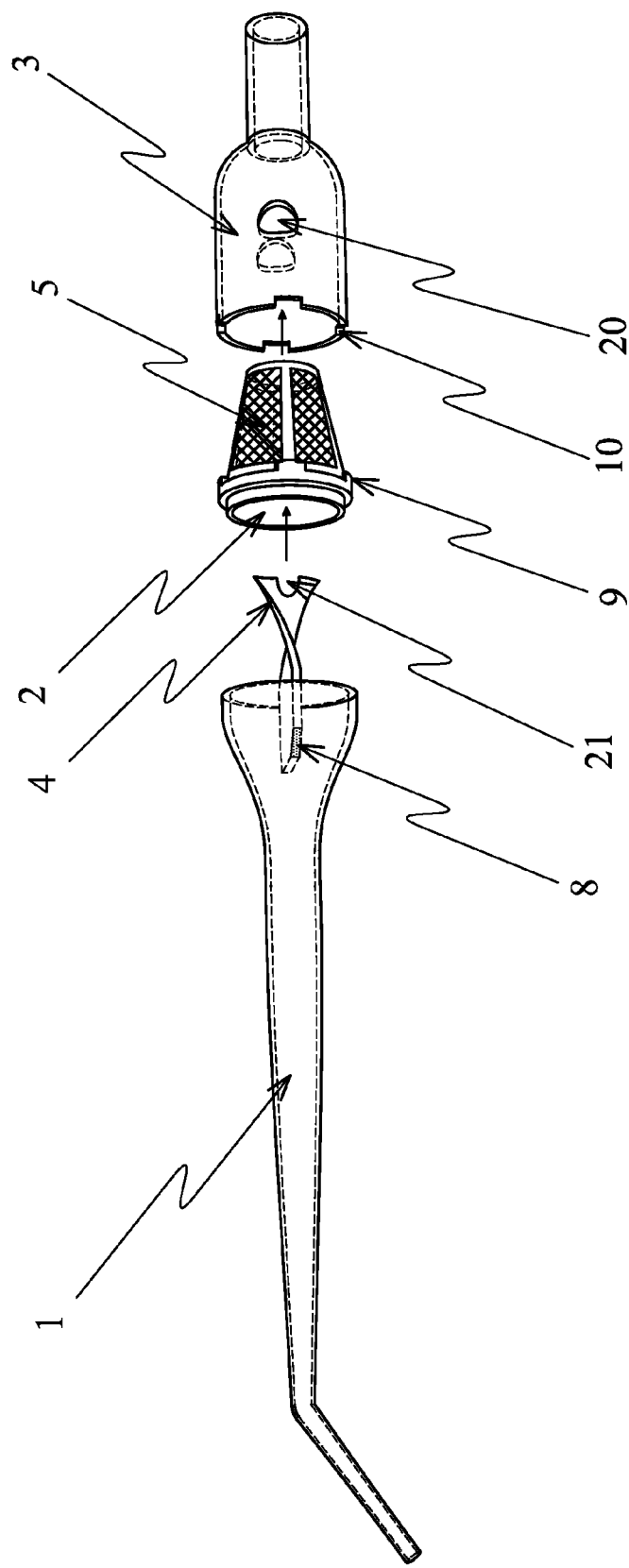
FIG. 1 is a perspective view of an embodiment of an autologous bone collecting device with constant suction efficiency of the invention.
Figure 2:
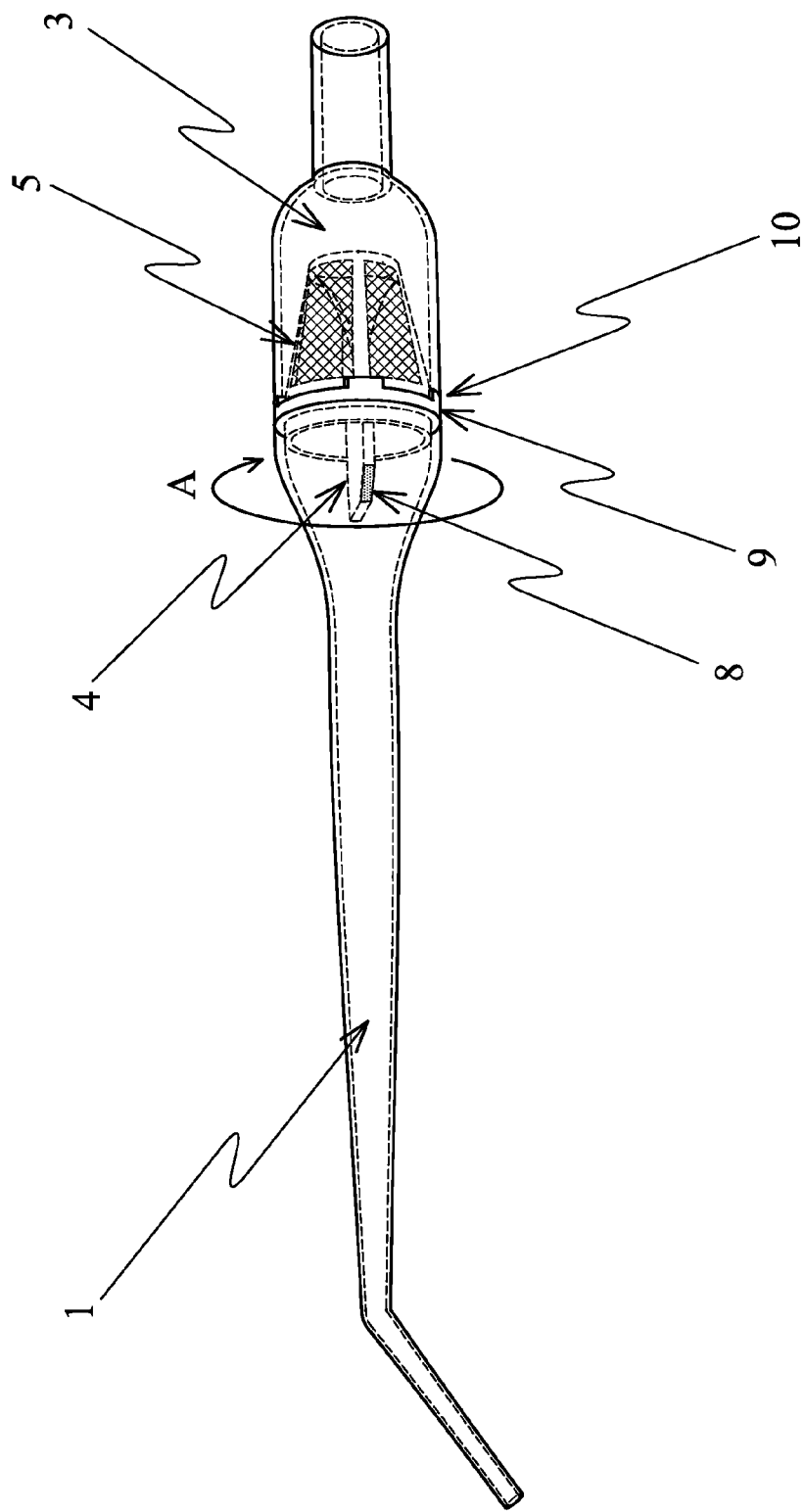
FIG. 2 is an exploded view of the autologous bone collecting device of FIG. 1.
Figure 3:
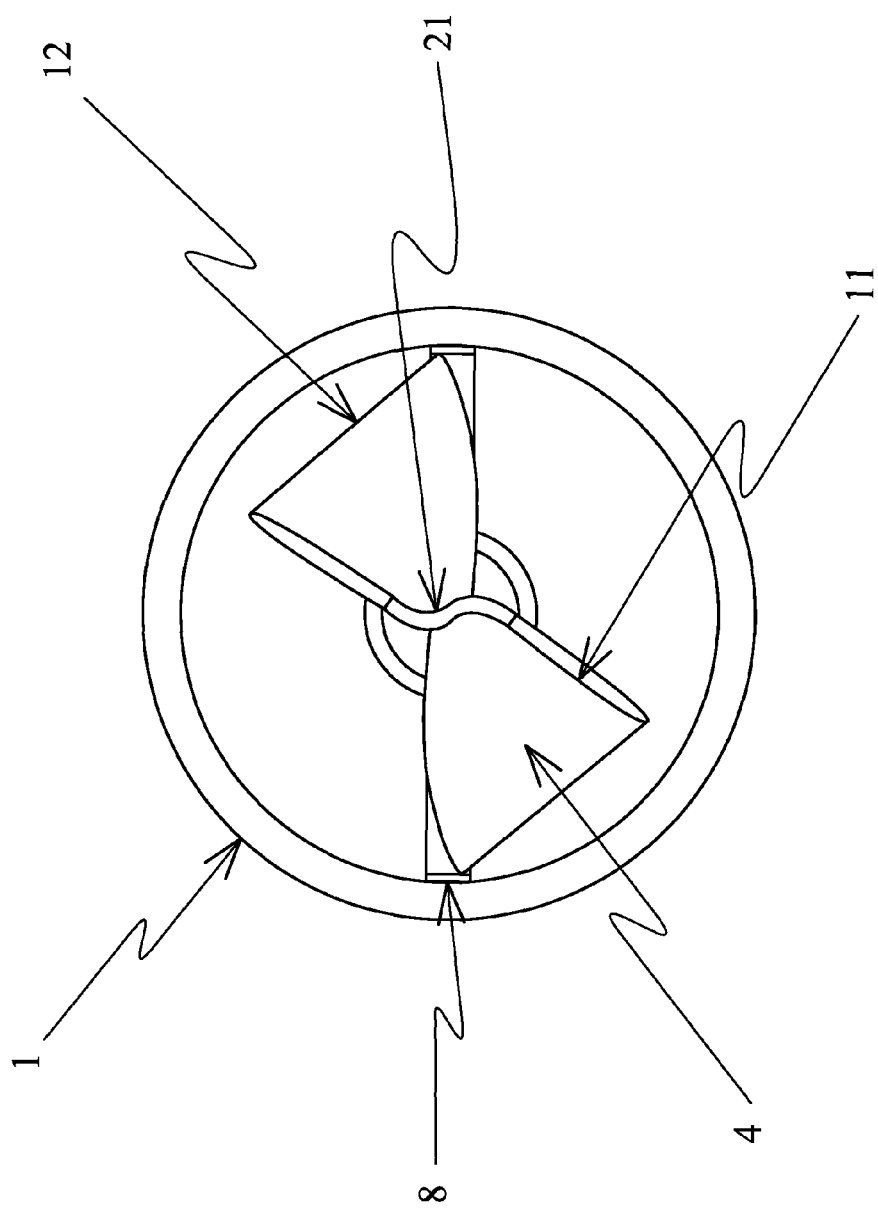
FIG. 3 depicts a blade disposed on an inner side of the suction nozzle side of the autologous bone collection device of FIG. 1.

FIG. 1 depicts an embodiment of an autogenous bone collecting device with constant suction efficiency of the invention. As shown in FIG. 1, the autogenous bone collecting device of the invention comprises, a blade 4 connected to a net 5 of a filter 2 fixed to a suction nozzle side 1. As shown in FIG. 2, the autogenous bone collecting device with constant suction efficiency of the invention comprises a suction nozzle side 1, wherein the blade 4 is fixed to the suction nozzle side 1, the filter 2 and a base 3. As shown in FIG. 3, the blade 4 has a spiral shape extending from the conjunction 8 and corresponding to the cross section of the bottom 11 of the filter 2 at an angle with respect to the axis of the filter 2. The base bottom 3 and filter 2 are connected to each other and relative rotation therebetween is prevented once the notch 9 is engaged with the slit 10. On the contrary, the suction nozzle side 1 is rotatably connected to the filter 2. In another embodiment of an autogenous bone collecting device with constant suction efficiency of the invention, a motor 14 drives a mechanism to rotate the wing in contact with the inner wall of the filter, in a similar manner to the previous described embodiment. The motor 14 is disposed within the suction nozzle side 1. Additionally, the rotation of the suction nozzle side 1, the base 3 and the filter 2 are prevented once the notch 9, the slit 18 and the slit 10 are engaged.

Embodiments of the autologous bone collection device with constant suction efficiency of the invention is described according to the drawings. In FIG. 1, the base 3 of an autologous bone collection device with constant suction efficiency is connected to a front of a vacuum device. The autologous bone collection device has a blade 4 on a part of the filter 2. The speckles of bone are collected from a non-implant site. When a required amount of speckles of bone is collected, the suctioned speckles of bone are stacked on a surface of the filter 2, thus, lowering suction efficiency. At this time, the base 3 connected to the filter 2 by an anti-rotation device and the slit 10 is held manually with one hand, and the suction nozzle side 1 in which the blade 4 is disposed is rotated with the other hand. Following blade 4 rotation, a contacting portion 12 of the spiral blade 4 moves the speckles of bone stacked on the surface of the filter to the bottom of the filter, thus, removing filter 2 obstruction.

Figure 4:
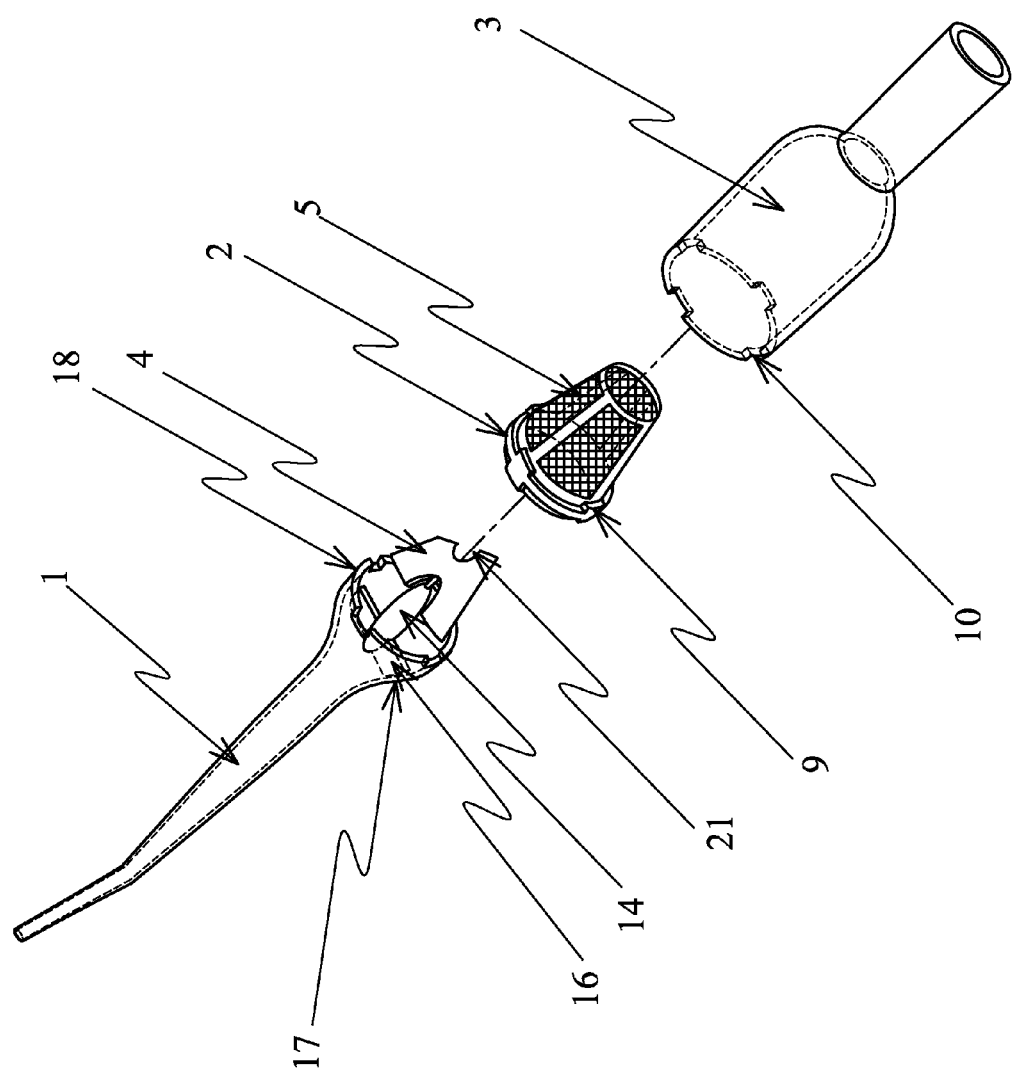
FIG. 4 is an exploded view of another embodiment of the autologous bone collecting device with constant suction efficiency driven by a motor.

In another embodiment of an autogenous bone collecting device with constant suction efficiency of the invention shown in FIG. 4, when the motor 14, fixed to a connecting portion 17 by a fixing plate 16 in the suction nozzle side 1, whereby the filter 2 and the base 3 is fixed by an anti-rotation mechanism, rotates the blade 4, the speckles of bone stacked on the surface of the filter are automatically moved to the bottom of the filter. With the motor mechanism able to automatically rotate constantly or frequently during usage, filter obstructions for the autogenous bone collecting device are removed without disrupting surgical operations.

Note that the obstructions on the surface of the filter are removed in the embodiment shown in FIGS. 1 and 3. The speckles of bone collected by rotation of the blade 4 contacting the inner wall of the filter 2 is moved in a predetermined direction by the contact angle guide of the blade 4 and the inner wall of the filter 2. As the speckles of bone are collected in a gap 21 between the blade 4 and the filter 2, removal of the speckles of bone from the gap is relatively easy.

Figure 5:
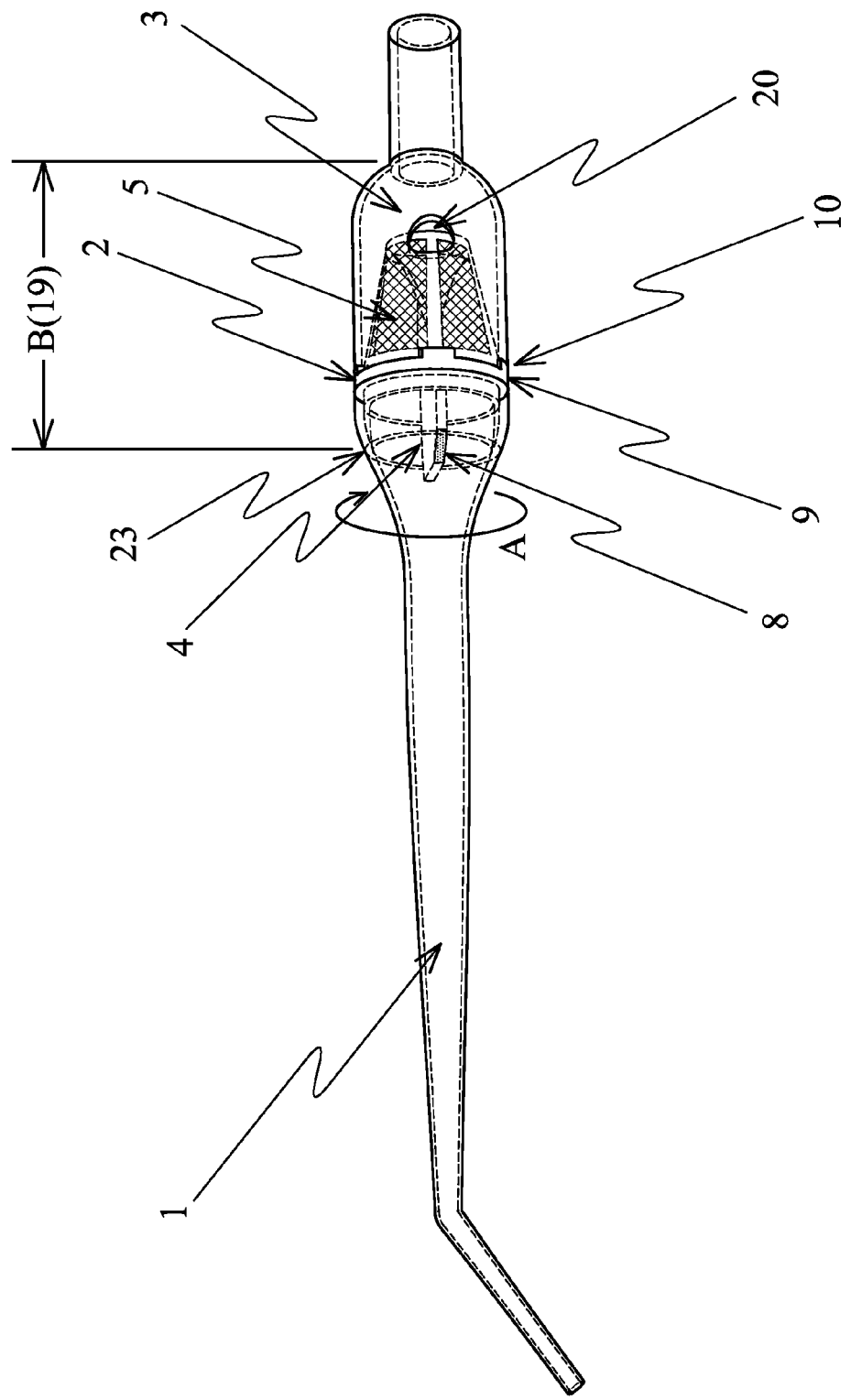
FIG. 5 depicts yet another autologous bone collecting device with constant suction efficiency of the invention, with the main body covered by a shrink film.

In yet another embodiment of an autologous bone collection device with constant suction efficiency of the invention shown in FIG. 5, an air leak hole 20 is formed on the lateral side of the autologous bone collection device. A shrink film 19 covers the B region and does not interfere with the rotating portion 23 of the blade 4 in the main body. With the filter 2 and the main body sealed, minimal air leakage results in increased suction force. However, when the autologous speckles of bone are collected, the filter 2 must be removed, thus, possibly damaging the shrink film 19 and the main body. Therefore, when the filter 2 is removed and the speckles of bone are collected, even if the main body is erected, air enters the main body via the air leak hole 20 to reduce the air-tightness, which causes no suction effect, thus, preventing possible repeated usage.

Meanwhile, all elements of the autologous bone collection device with constant suction efficiency of the invention are not limited to the embodiments in the Figs. The material and shapes of all elements can be appropriately modified without exceeding the scope of the invention. Additionally, to identify the stacked speckles of bone on the surface of the filter or movement thereof, it is preferred that the material of the main body is of high transparency material. Moreover, amount of blades of the blade is dictated by the suction efficiency of the autologous bone collection device. Although the blade, as shown in FIG. 3, has two symmetrical blades with respect to the axis of the filter, the blade can also have a plurality of blades. Similarly, the contacting portion can be of any shape as long as motion with respect to the axis of the filter can be maintained. The shape of the contacting portion can be modified to any shape within the scope of the invention, and is not limited to a linear shape or a curved shape.

Also, the autologous bone collection device with constant suction efficiency of the invention can be applied to a machine with a system for collecting speckles of bone by a filter in an autologous bone implantation operation.

Meanwhile in practice, for the non-implant site, to collect the largest amount of speckles of bone from the smallest area for minimal surgical invasiveness, a filter having a mesh is efficient in collecting the most speckles of bone. However, when a small mesh is utilized, the filter is easily obstructed by the speckles of bone during collection, which causes low suction efficiency. In this example, it would be necessary to frequently change the filter or remove the speckles of bone stacked on the surface of the filter during the surgical operation. For the autologous bone collection device with constant suction efficiency of the invention, collection of the speckles of bone require a relatively shorter period of time, as the speckles of bone are moved to one location at the bottom of the filter, easily accessed following twisting of the main body by 180° during surgical operation. In the first embodiment, even for surgical operations requiring a short period of time, suction during surgical operations using the autologous bone collection device will be disrupted. In the second embodiment, since the autologous bone collecting device of the invention has a motor mechanism rotating the blade, the blade is constantly or frequently rotating during surgical operations. The continued or frequent suction allows collected speckles of bone to be pushed to the bottom of the filter without interrupting the surgical operation. The autologous bone collecting device can be applied to surgical operation categories ranging from plastic operations for fingers to bone graft operations.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An autogenous bone collection device used along a suction path to suction objects such as cooling liquid, speckles of bone, saliva and blood, wherein after the speckles of bone are suctioned, the speckles of bone are separated from the other objects by a filter, comprising:
   a blade rotatably contacting an inner wall of the filter, and the blade rotated to move obstructions stacked on a surface of the filter in an arbitrary direction to remove the obstructions of the filter, whereby suction efficiency is held constant; and
   a suction nozzle side rotatably connected to the filter.

2. The autogenous bone collection device as claimed in claim 1, wherein the blade is fixed to a main body and rotated by a motor to move obstructions stacked on a surface of the filter in an arbitrary direction, to remove the obstructions of the filter, whereby suction efficiency is held constant.

3. The autogenous bone collection device as claimed in claim 1, wherein the speckles of bone collected in the filter are collected in an arbitrary position of the filter by rotating the blade, which contacts the inner wall of the filter.

4. The autogenous bone collection device as claimed in claim 1, wherein the autogenous bone collection device comprises a main body partially or entirely covered by a shrink film to prevent junction air leakage, the main body having an integrally formed air leak hole covered by the shrink film, and the shrink film not obstructing the rotation of the blade.

5. An autogenous bone collection device comprising:
   a filter having an inner wall;
   a blade, rotatably connected to the filter, contacting the inner wall of the filter, wherein the blade is rotated to remove obstructions on the filter; and
   a suction nozzle side rotatably connected to the filter.

6. The autogenous bone collection device as claimed in claim 5, further comprising:
   a motor, driving the blade, connected to the suction nozzle side.

7. The autogenous bone collection device as claimed in claim 6, further comprising:
   a base, wherein the filter is connected between the suction nozzle side and the base; and
   a shrink film covering the base.

8. The autogenous bone collection device as claimed in claim 5, wherein the filter has a net, and the blade has a contacting portion pressing against the net while rotating.

9. An autogenous bone collection device, comprising:
   a suction nozzle side;
   a base, configured to connect to a vacuum source and defining a suction path from the suction nozzle side to the base;
   a filter, connected between the suction nozzle and the base, wherein the suction nozzle side is rotatable relative to the filter; and
   a blade rotatably disposed in the filter, arranged such that during rotation thereof the blade contacts an inner wall of the filter so as to remove obstructions collected on the inner wall of the filter.

* * * * *